(12) United States Patent
Ritland (10) Patent No.: US 7,753,910 B2
(45) Date of Patent: Jul. 13, 2010

(54) SURGICAL IMAGE TRACKER MOUNTING BASE APPARATUS AND METHOD OF USE

(76) Inventor: Stephen Ritland, 1150 N. San Francisco St., Flagstaff, AZ (US) 86001

( * ) Notice: Subject to any disclaimer, the term of this patent is extended or adjusted under 35 U.S.C. 154(b) by 996 days.

(21) Appl. No.: 10/624,234

(22) Filed: Jul. 21, 2003

(65) Prior Publication Data

US 2005/0020920 A1     Jan. 27, 2005

(51) Int. Cl.
   *A61B 17/56*     (2006.01)
(52) U.S. Cl. ........................................................ 606/53
(58) Field of Classification Search .................. 606/61, 606/97, 130, 53, 86 R, 87, 96, 102, 246, 426, 606/459; 411/140, 393
See application file for complete search history.

(56) References Cited

U.S. PATENT DOCUMENTS

| | | | | |
|---|---|---|---|---|
| 2,825,329 A | * | 3/1958 | Caesar | 606/71 |
| 4,651,724 A | * | 3/1987 | Berentey et al. | 606/69 |
| 5,197,966 A | * | 3/1993 | Sommerkamp | 606/69 |
| 5,487,741 A | * | 1/1996 | Maruyama et al. | 606/60 |
| 6,203,543 B1 | * | 3/2001 | Glossop | 606/60 |
| 6,932,823 B2 | * | 8/2005 | Grimm et al. | 606/130 |
| 2003/0078565 A1 | * | 4/2003 | Vilsmeier et al. | 606/1 |
| 2004/0172044 A1 | * | 9/2004 | Grimm et al. | 606/130 |

OTHER PUBLICATIONS

Web pages, http://www.brainlab.com, Apr. 2, 2002; 5 pp.

* cited by examiner

*Primary Examiner*—Eduardo C Robert
*Assistant Examiner*—David Comstock
(74) *Attorney, Agent, or Firm*—Holme Roberts & Owen LLP (57) ABSTRACT

A device is presented for temporarily mounting an image tracker to a patient during surgery. The device preferably includes a first aperture and a axially-align second aperture. The apertures are sized to receive a securing mechanism, such as a bone screw that is temporarily inserted into a patient's bone for holding the image tracker near the vicinity of a surgical site. The device further preferably includes at least one projection such as a pin to stabilize the device from rotating.

13 Claims, 9 Drawing Sheets

SURGICAL IMAGE TRACKER MOUNTING BASE APPARATUS AND METHOD OF USE

FIELD OF THE INVENTION

The present invention is a device and method of use for an apparatus used to mount an image tracker to a patient.

BACKGROUND AND SUMMARY OF THE INVENTION

Due to the frequently limited amount of exposure of the spine or interior surgical area, spinal implant procedures lend themselves to use of image guidance for surgery. Examples of such image guidance systems include the BrainLAB. System and the Stealth System. The image guidance systems use data from standard CT or MRI scans to build a three dimensional image of the patient's spine. This model is then electronically matched to the patient's anatomy during surgery, allowing the surgeon, in effect, to see through tissue in order to accurately determine the placement of instruments or devices. During the operation, sensitive structures such as blood vessels and nerves, which the surgeon wants to avoid on the way to the anatomical target, can be visualized. In addition, during the operation the surgeon can follow the movements of his or her instruments on the computer screen in real time.

As understood by those skilled in the art, these image guidance systems utilize a computer system with a monitor and two cameras that emit infrared signals, thereby determining the patient's position in the operating room as well as the position of the surgical instruments in relation to the patient's spine. The infrared signals are continuously monitored during surgery using an image tracker receiver that is located in the vicinity of the surgical site.

The present invention comprises a mounting base for mounting an image tracker into a bone of a patient. The mounting base includes a securing mechanism, such as a bone screw, that is inserted through the base and then into the bone. The mounting base also includes at least one projection to further stabilize the mounting base and assist in preventing rotation of the mounting base after attaching the mounting base to the patient. The image tracker array is interconnected to the secured mounting base, thereby providing a secure mounting apparatus that can be used in the immediate vicinity of the patient's surgical site. Thus, in one aspect of the present invention, a device for stabilizing an image tracker in a patient's bone is provided, where the device comprises a securing mechanism and a body, where the body has a first aperture and a second aperture both sized to receive the securing mechanism. In use, the securing mechanism is inserted through the first aperture and the second aperture and inserted into the patient's bone for temporarily stabilizing the image tracker to a patient.

A projection is also preferably used to prevent the device from rotating after inserting the securing mechanism into the patient's bone. Thus, it is a separate aspect of the present invention to provide a mounting base for stabilizing an image tracker in a patient's bone, wherein the device comprises a body having an entrance aperture and an exit aperture and a passageway therebetween. In addition, the device includes means for securing the base to the patient's bone, and wherein the means for securing is sized to be received in the passageway. The device further includes a means for stabilizing the body from rotating. In use, the means for securing is inserted through the entrance aperture, the passageway, and the exit aperture and inserted into the patient's bone for temporarily stabilizing the image tracker to a patient.

A method of using the device is also provided. Thus, it is a separate aspect of the present invention to provide a method of attaching an image tracker to a patient, wherein the method comprises a) inserting a bone screw through a body of a mounting base, the body having an entrance aperture, an exit aperture, and at least one stabilizing projection; b) advancing the bone screw into a bone of the patient; and c) tightening the bone screw into the bone.

Further and more specific advantages and features of the invention will become apparent to those skilled in the art from the following detailed description, taken in conjunction with the drawings.

DETAILED DESCRIPTION OF THE INVENTION

Referring to FIGS. 1-4, a first embodiment of the mounting base 10 comprising the present invention is shown. The mounting base 10 includes a body 12 having a first or entrance aperture 14 for receiving a securing mechanism 16. Mounting base 10 further includes a second or exit aperture 18 axially aligned with the entrance aperture 14 also for receiving securing mechanism 16. A securing mechanism passageway 20 extends through body 12 between entrance aperture 14 and exit aperture 18 for allowing securing mechanism 16 to be extended through body 12 of base 10.

Preferably, securing mechanism 16 is a 4 to 8 mm diameter bone screw having a plurality of threads 22 along at least the lower portion of its exterior. When a bone screw is used as securing mechanism 16, it serves to anchor the base 10 to a bone, such as the iliac crest of the pelvis. The threads 22 of securing mechanism 16 allow securing mechanism 16 to be inserted into a bone and rotated until a relatively tight insertion is achieved.

Figure 1:
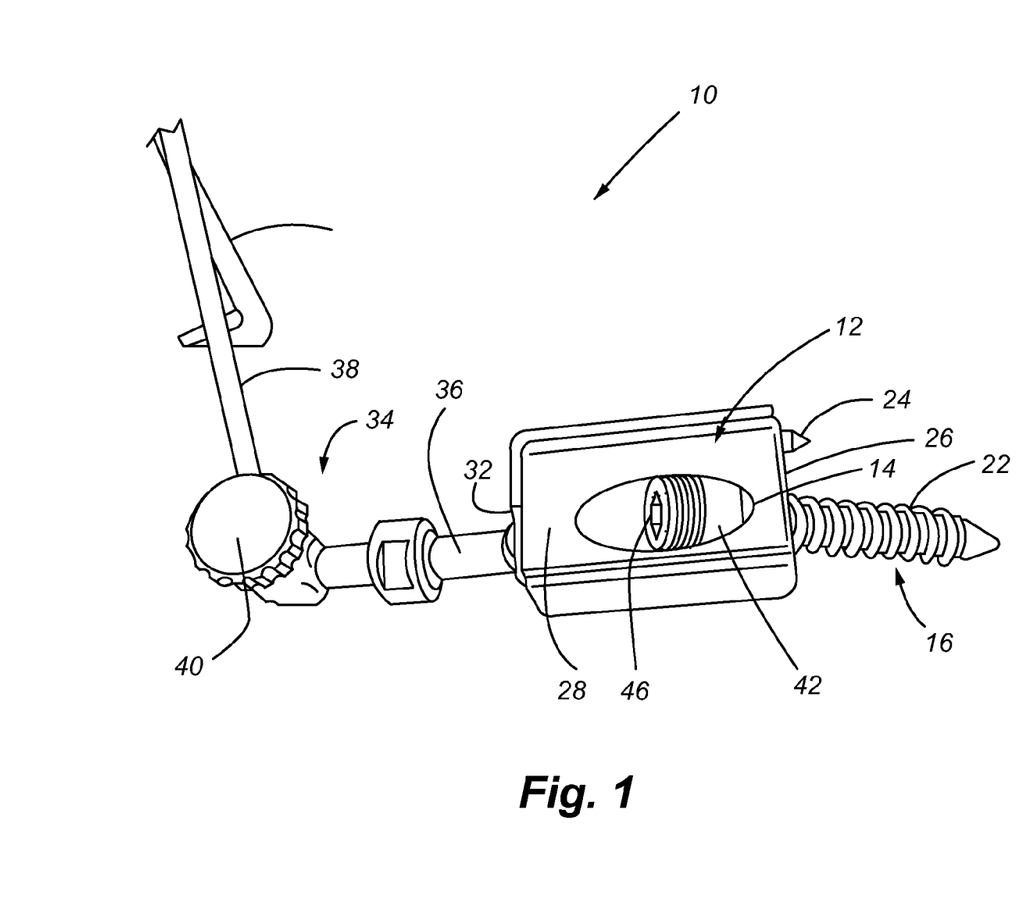
FIG. 1 is a perspective view of a first embodiment of the present invention wherein the securing mechanism passes through a side and bottom surface of the body of the mounting base.
Figure 2:
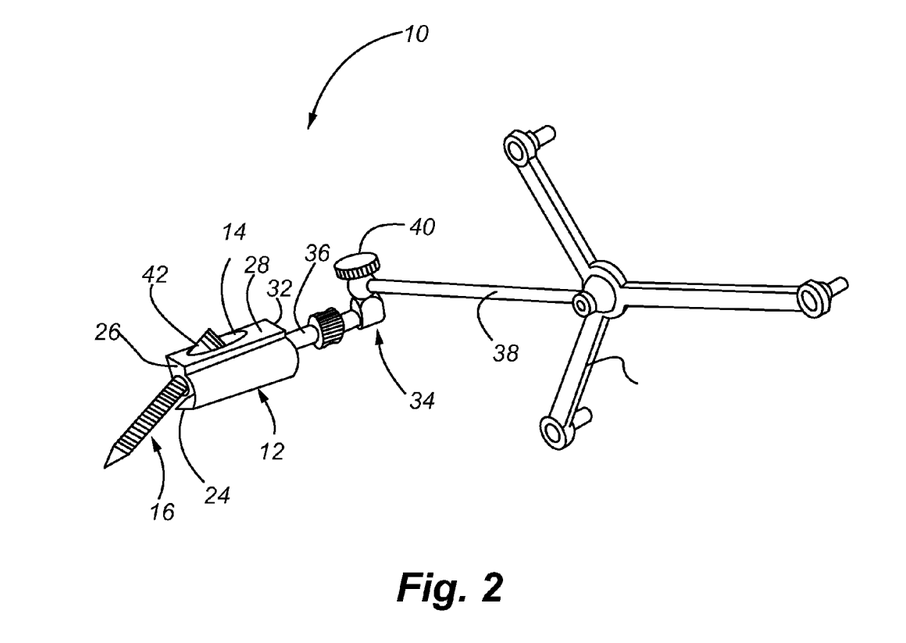
FIG. 2 is a second perspective view of the device shown in FIG. 1.
Figure 3:
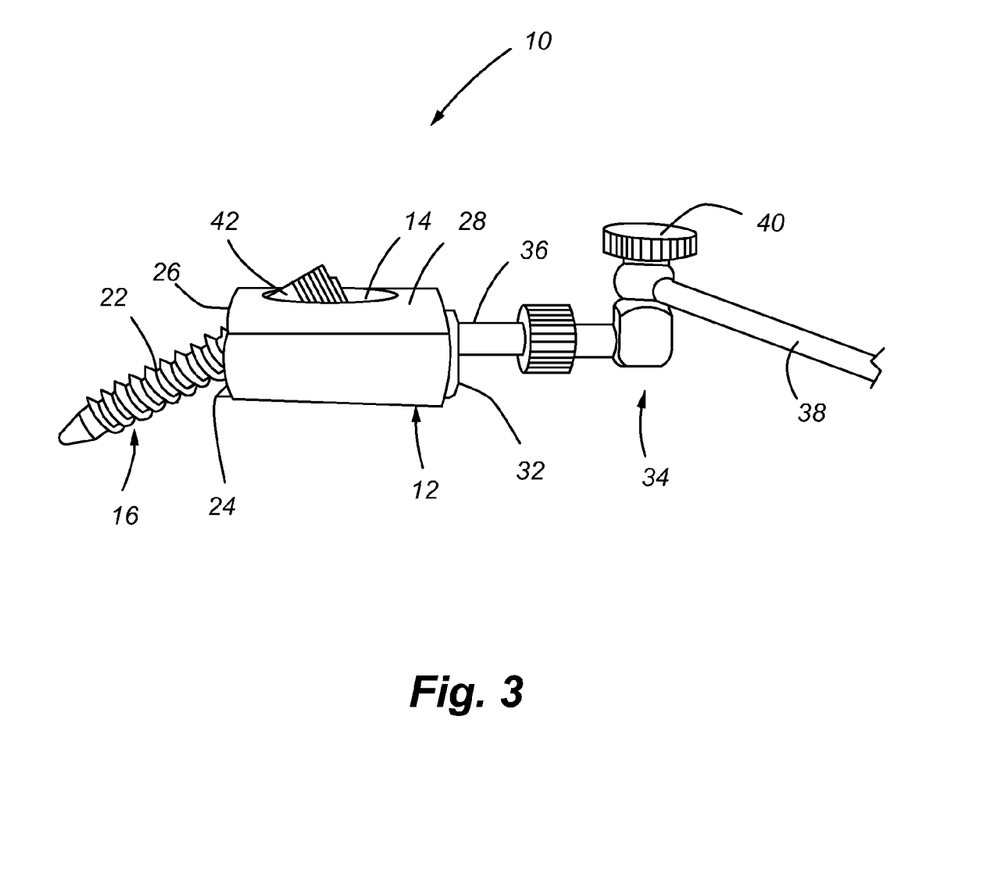
FIG. 3 is a third perspective view of the device shown in FIG. 1.
Figure 4:
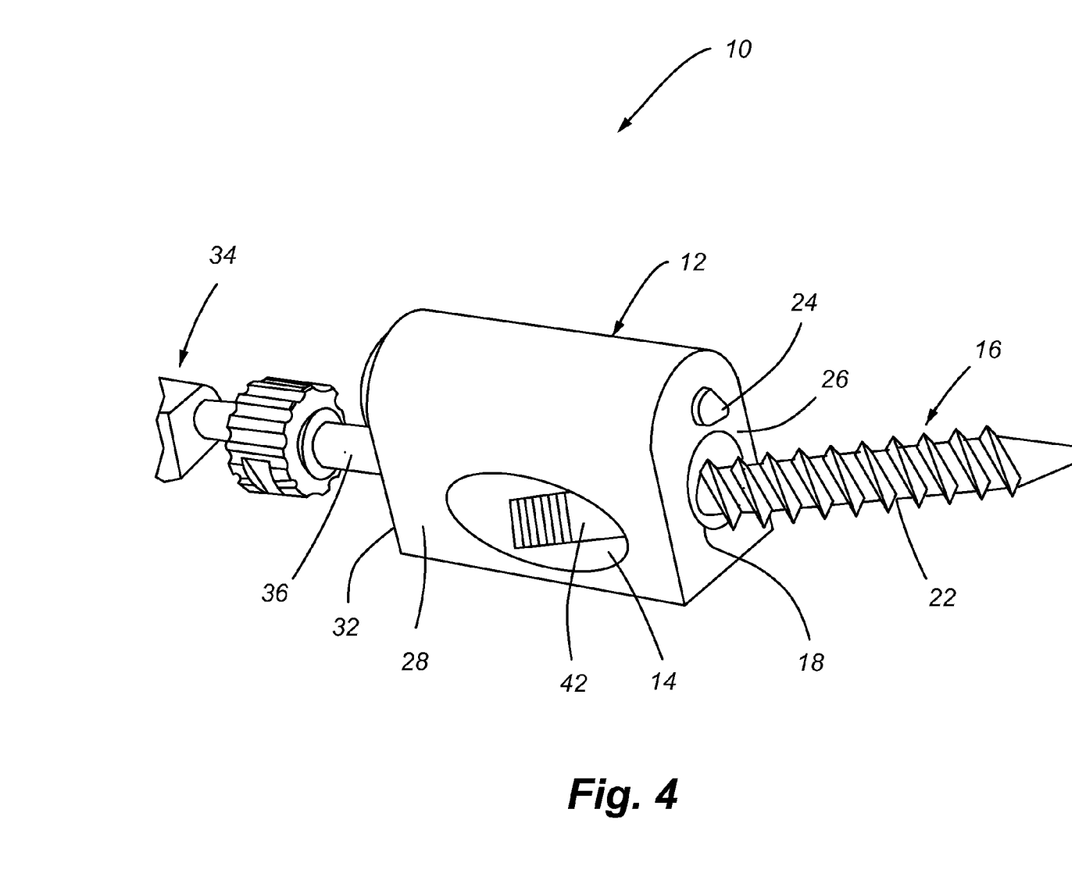
FIG. 4 is a fourth perspective view of the device shown in FIG. 1.
Figure 5:
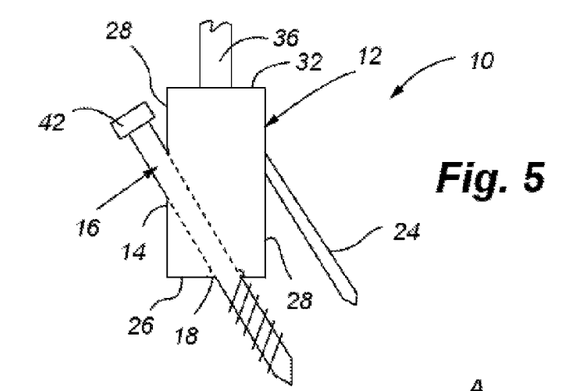
FIG. 5 is a side elevation view of a modification of the first embodiment wherein the mounting base includes a projection mounted on a side of the body of the mounting base.

Mounting base 10 preferably includes at least one projection 24 to provide stability to base 10 during use. Projection 24 preferably takes the form of a small rod, a point, a pin, or other structure that serves to prevent rotational movement of base 10 while base 10 is anchored to an object, such as a patient's hip bone. To prevent rotational movement, projection 24 is preferably laterally offset from securing mechanism 16 and/or exit aperture 18, thereby providing rotational stability to base 10 upon tightening securing mechanism 16 into bone. As shown in FIGS. 1-4, the projection 24 is preferably located on the bottom surface 26 of base 10. However, as shown in FIG. 5, projection 24 could be located to a side 28 of the body 12 of base 10 where it extends generally in the direction of the bottom surface 26 of base 10. In this arrangement, the length of projection 24 preferably is such that it extends beyond the bottom surface 26 of base 10 if mounted into a relatively flat bone, or otherwise extends a sufficient distance to intercept a bodily structure that rotationally stabilizes the base 10.

Figure 6:
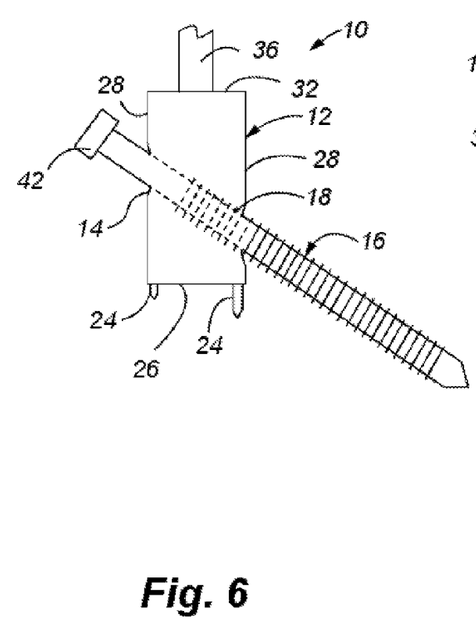
FIG. 6 is a side elevation view of another modification of the first embodiment wherein the mounting base includes a plurality of projections and a securing mechanism that passes through the sides of the body of the mounting base.
Figure 7:
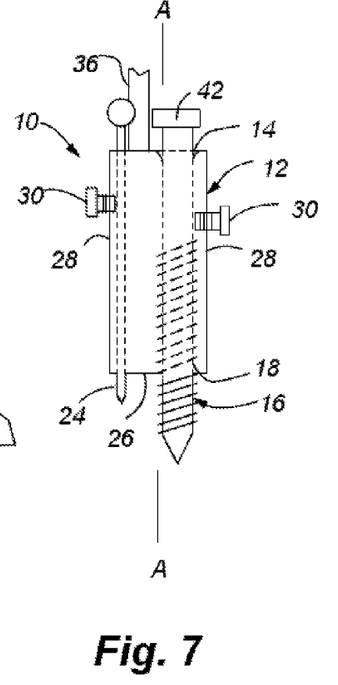
FIG. 7 is a side elevation view of another modification of the first embodiment wherein the mounting base includes a retractable and detachable projection, and a securing mechanism that passes through the top and bottom surfaces of the mounting base.

Referring now to FIG. 6, a plurality of projections 24 may be used. Furthermore, projection 24 may be of various lengths as also shown FIG. 6. The projection 24 can be permanently fixed to body 12 of base 10. Alternatively, as shown in FIG. 7, projection 24 may be detachable and adjustable. For example, FIG. 7 illustrates a mounting base 10 where the securing mechanism 16 is located offset from the longitudinal center axis A-A of the body 12, and where a projection 24 in the form of a small rod or pin that extends through the body 12 is illustrated. Here, the projection 24 can be inserted separately from the securing mechanism 16 and the projection 24 can be optionally secured with a set screw 30, and then removed upon completion of using the mounting base 10. Thus, the projection 24 can be retractable within and/or removeable from the body 12.

Still referring to FIG. 7, in a separate aspect of the invention, a set screw 30 may also be used for temporarily securing the securing mechanism 16 in the body 12 of mounting base 10. More particularly, for all embodiments and their modifications described herein, the securing mechanism 16 may be optionally secured within the body 12 using a set screw 30.

Figure 8A:
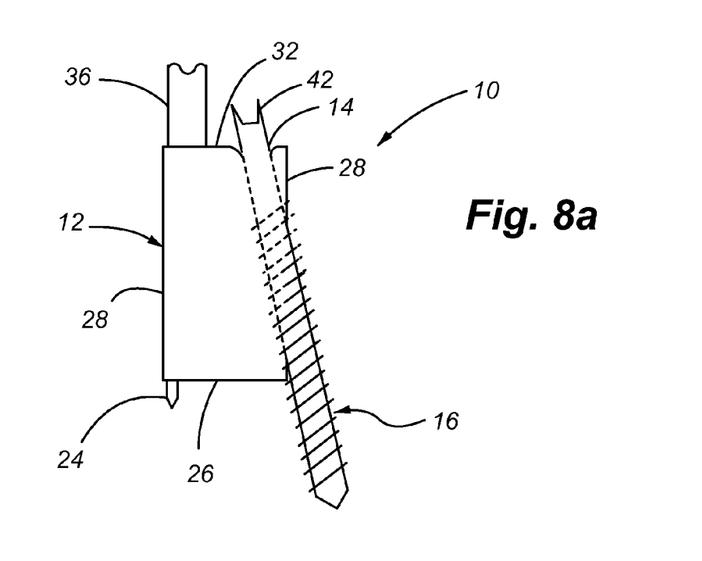
FIGS. 8a and 8b are side elevation views of modifications of the first embodiment wherein the mounting base includes a securing mechanism that passes through the top and through a side of the body of the mounting base.
Figure 8B:
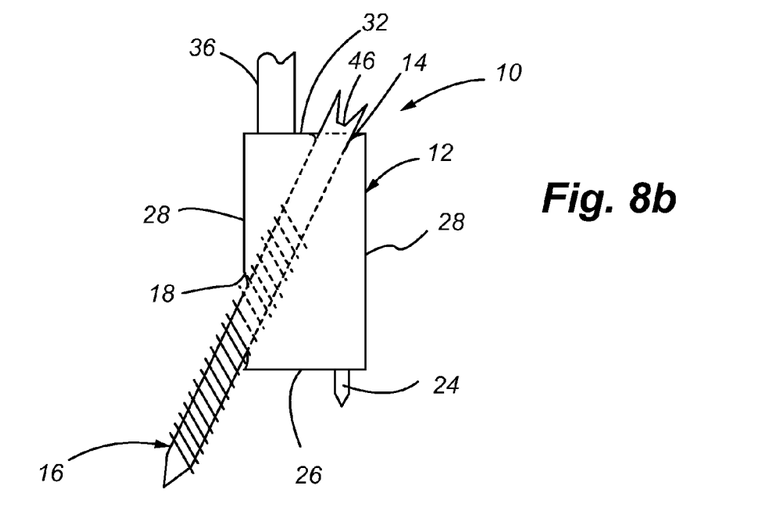

In a separate aspect of the invention, entrance aperture 14 and exit aperture 18 can be positioned along different surfaces of base 10. More particularly, for the mounting base 10 shown in FIGS. 1-5, the first or entrance aperture 14 is situated along a side face 28 of the body 12 of base 10, and the second or exit aperture 18 is located along the bottom surface 26 of the base 10. Alternatively, as shown in FIG. 6, the entrance aperture 14 may be located along a lateral side 28, and the exit aperture 18 may also be located on a lateral side 28. In yet another alternative arrangement, as shown in FIG. 7, the entrance aperture 14 may be located along the top surface 32 of base 10, while the exit aperture 18 is located along the bottom surface 26. In yet another alternative arrangement, as shown in FIGS. 8a and 8b, the entrance aperture 14 may be located along the top surface 32, while the exit aperture 18 is located along a lateral side 28 of body 12. Thus, during manufacture of base 10, the orientation if passageway 20 can be modified to provide different orientations for the securing mechanism 16 relative to body 12, thereby allowing bases 10 to be used for different body locations and different body positions that may be desirable during a given surgical procedure.

Mounting base 10 preferably includes a mechanism for receiving image tracker array T. One preferred arrangement for such a mechanism is a support structure 34 for receiving the image tracker array T. Support structure 34 preferably includes a permanently mounted post 36 that may be used to detachably attach an image tracker array. T using an interconnecting rod 38. As shown in FIGS. 1-4, the interconnecting rod 38 is preferably secured to post 36 using tightening screw 40. Post 36 can be attached to the top surface 32 of body 12 of mounting base 10, or the support structure 34, including post 36, can be on the side 28 of body 12 of mounting base 10, as shown in FIG. 9.

Figures 9, 10, 11:
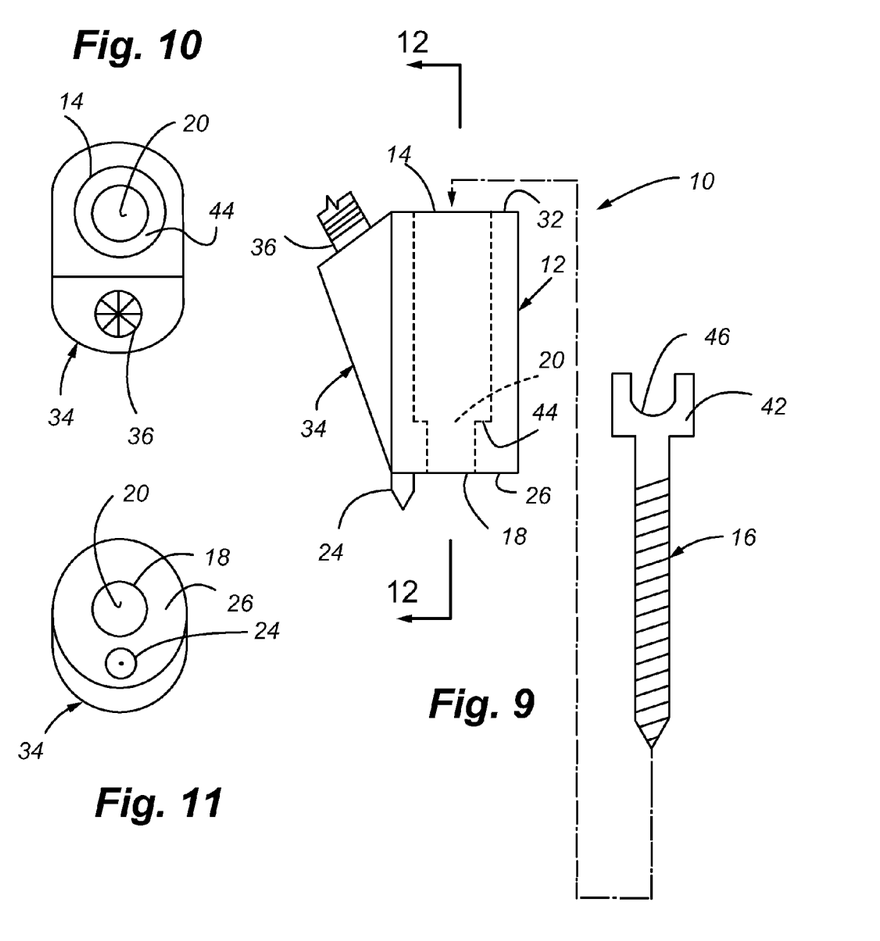
FIG. 9 is an exploded side elevation view of another modification of the first embodiment wherein the mounting base includes an inner flange and a side mounted connector for the tracker array.
FIG. 10 is a plan view of the top of the device shown in FIG. 9.
FIG. 11 is an elevation view looking at the bottom of the device shown in FIG. 9.
Figure 12:
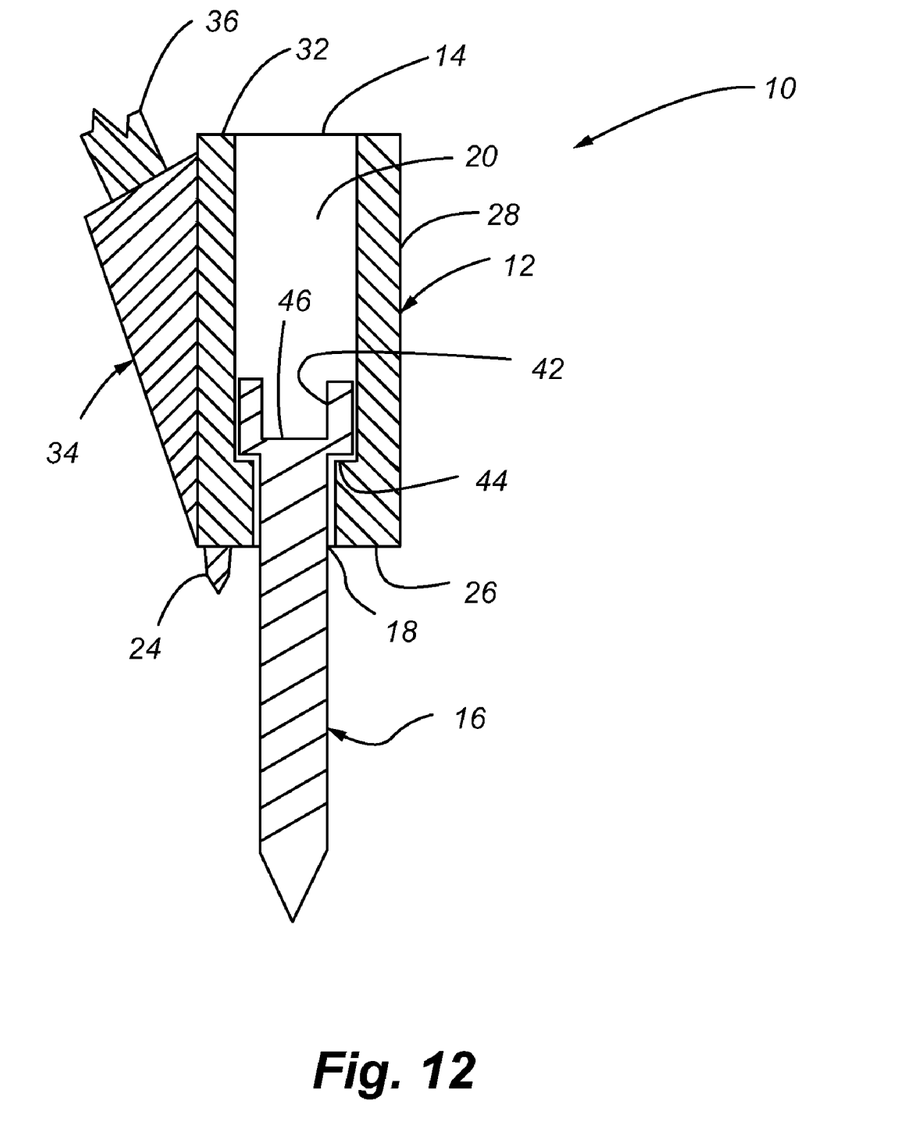
FIG. 12 is a cross-sectional view of the device shown in FIG. 9 taken along line 12-12.

Referring now to FIGS. 9-12, yet a alternative modification to the first embodiment of the present invention is shown, wherein mounting base 10 includes a body 12 having a passageway 20 that receives the securing mechanism 16 including its head portion 42, and wherein the head portion 42 of securing mechanism 16 can extend into the passageway until contacting an inner flange or protrusion 44 within the passageway 20. Thus, protrusion 44 provides mechanism for limiting the depth with which securing mechanism 16 can be driven into the patient's bone. More particularly, if a bone screw is used as the securing mechanism 16, then the bone screw can only be driven until the head portion 42 contacts the protrusion 44. Thus, this feature acts as a safety device for limiting the penetration depth of the securing mechanism 16. It is to be understood that the location of the protrusion 44 in the passageway 20 maybe positioned closer to the bottom surface 26 of body 12 than the upper surface 32 of body 12, as shown in FIG. 10, or the position of the protrusion 44 may located equidistant between the bottom surface 26 and upper surface 32, or closer to the upper surface 32 than the bottom surface 26. However, it is preferable to maintain a length of the securing mechanism 16 within the body 12 to effectively maintain alignment of the body 12, with the shaft of securing mechanism 16.

Figure 13A:
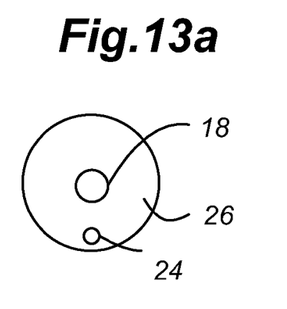
FIGS. 13a-f are elevation views of the bottom surfaces of different shaped and differently configured mounting bases.
Figure 13B:
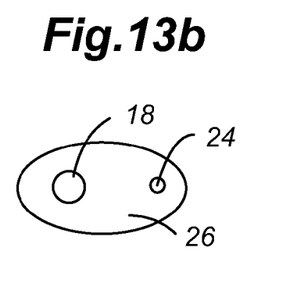
Figure 13C:
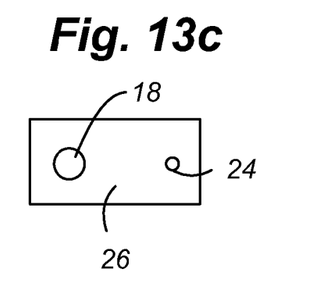
Figure 13D:
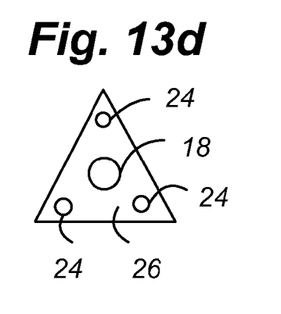
Figure 13E:
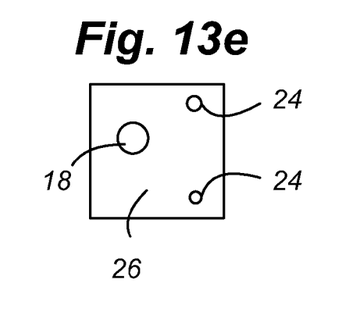
Figure 13F:
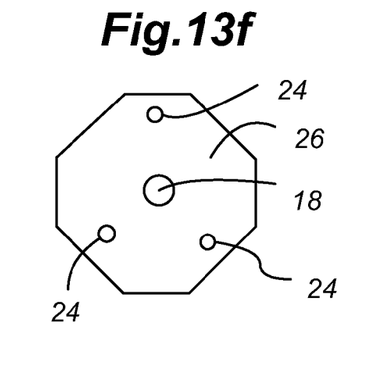

Referring now to FIGS. 13a-13f, the bottom surface of different possible shapes of mounting bases 10 are depicted, together with a number of different arrangements for the location of the exit aperture 18 and projection(s) 24. More specifically, FIG. 13a depicts a mounting base having a circular shaped bottom surface, with a centrally located exit aperture 18 and a single projection 24 located near the outer edge of the bottom surface 26. FIG. 13b depicts an oval shaped mounting base 10, and FIG. 13c depicts a rectangular shaped mounting base 10, where both of the bottom surfaces 26 include a single projection 24. FIG. 13d depicts a triangular shaped bottom surface 26 with three projections 24, and wherein the exit aperture 18 is situated substantially in the center of the bottom surface 26 with the projections 24 evenly distributed near the corners of the bottom surface 26. FIG. 13e illustrates a square shaped bottom surface 26, and FIG. 13f depicts a hexagonally shaped bottom surface 26, both having a plurality of projections 24. Thus, a variety of cross sections and configurations are available for the mounting base 10.

In a separate aspect of the invention, a mounting base 10 may have a plurality of securing mechanisms 16 (not shown) that are used to penetrate the bone and anchor the mounting base.

In use, a surgeon decides upon a point for locating the base 10, and thus, the image tracker array T. Image tracker array T is typically located at a position situated near the surgical incision point on the patient, but spaced apart a sufficient distance such that the base 10 is not too close to the incision point so as to interfere with the surgeon's access and motion during surgery. The position for the image tracker base 10 is then properly prepared, which may typically include sterilization of the point of placement. A securing mechanism 16, such as a bone screw, is then threaded through both the first or entrance aperture 14 and second or exit aperture 18 of the body 12. Subsequently, while the securing mechanism 16 is still threaded through body 12, the securing mechanism 16 is then inserted into the patient's bone. The securing mechanism 16 preferably includes a tool slot 46 or receptacle along its top surface for receiving a tool, such as a surgical screwdriver. The securing mechanism 16 is tightened into the bone so as to provide a relatively tight fit with the bone within which it is inserted. During the installation of the securing mechanism 16, if projection 24 is permanently affixed to the mounting base 10, the projection 24 seats into the patient's bone or tissue to prevent rotation of the mounting base 10 and assist in stabilizing the mounting base 10. Alternatively, if the projection 24 is detachably or retractably attached to the mounting base 10, then an additional step of advancing the projection 24 is performed to seat the projection into the patient's bone or tissue to prevent rotation of the mounting base.

All components of the invention described herein are manufactured of a material appropriate for surgical use. For example, the components can be made of stainless steel. However, it is to be understood that other types of materials may also be used, such as titanium or ceramics.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A surgical aid assembly for attachment to a bone of a patient, the patient further having a tissue, the surgical aid assembly comprising:
    a securing mechanism, wherein said securing mechanism consists of only one bone screw;
    a body having a first surface longer than a second surface, wherein the first surface is parallel to a longitudinal axis of the body, and the body having a first aperture on the first surface and a second aperture on the second surface both sized to receive said securing mechanism, wherein an axis is disposed along a passageway between the first aperture and the second aperture, further wherein the axis of the passageway obliquely traverses the longitudinal axis of the body, and wherein the securing mechanism is inserted through the first aperture and the second aperture and inserted into the patient's bone for temporarily stabilizing the image tracker to the patient's bone;
    an attachment point disposed on the body for attaching an image tracker to the body;
    at least one stabilizing projection to seat the body to the patient's bone or tissue, wherein the at least one stabilizing projection is positioned on the second surface of the body; and
    an inner flange within the passageway between the first aperture and the second aperture.

2. The surgical aid assembly of claim 1, wherein the at least one stabilizing projection includes a pin that is removably attachable to the body, the pin being securable to the body by a set screw associated with the body.

3. The surgical aid assembly of claim 1, wherein the attachment point includes a mounting post disposed on said body and operable to releaseably attach the image tracker to said body.

4. A surgical aid assembly for attachment to a patient's bone, comprising:
    an image tracker;
    a mounting base for stabilizing the image tracker, the mounting base including a body having a longitudinal axis, and having an entrance aperture and an exit aperture and a passageway therebetween; wherein the passageway has a central axis that obliquely traverse the longitudinal axis of the mounting base;
    means for securing the base to the patient's bone, wherein said means for securing is sized to be received in said passageway, wherein the means for securing is inserted through the entrance aperture, the passageway, and the exit aperture and inserted into the patient's bone for temporarily stabilizing the image tracker;
    means for stabilizing the body from rotating; and
    means for attaching the image tracker to the body; and
    an inner flange within the passageway.

5. The surgical aid assembly of claim 4, wherein said means for stabilizing comprises at least one projection.

6. The surgical aid assembly of claim 5, wherein said at least one projection is positioned on a bottom surface of said body.

7. The surgical aid assembly of claim 5, wherein said at least one projection comprises a pin.

8. The surgical aid assembly of claim 4, wherein the means for stabilizing includes a pin that is removably attachable to the body, the pin being securable to the body by a set screw associated with the body.

9. The surgical aid assembly of claim 4, wherein the means for attaching includes a mounting post disposed on said body and operable to releaseably attach the image tracker to said body.

10. A surgical aid assembly for attachment to a patient's bone, comprising:
    an image tracker;
    a device for stabilizing the image tracker to the patient's bone, the device including a body comprising:
        a plurality of surfaces comprising:
            a top surface;
            a bottom surface;
            a first side surface; and
            a second side surface, wherein the first side surface and second side surface are longer than the top surface and bottom surface and wherein a longitudinal axis is parallel with the first side surface;
        a first aperture disposed on said top surface;
        a second aperture disposed on at least one of the surfaces selected from the group consisting of:
            said first side surface; and
            said second side surface;
        a passageway between said first and second apertures, the passageway having an inner flange, an axis and a set screw operable with the passageway to secure said bone screw in place within the passageway, wherein the axis of the passageway obliquely traverses the longitudinal axis of the body and
    a projection disposed on at least one of the surfaces selected from the group consisting of:
        said second side surface of said body; and
        said bottom surface of said body;
    a mounting post disposed on said body and operable to releaseably attach the image tracker to said body; and
    a securing mechanism consisting of a single bone screw;
    wherein said first and second apertures are both sized to receive said bone screw; and wherein said bone screw is adapted to be inserted through said passageway and into the patient's bone for temporarily stabilizing the image tracker.

11. The surgical aid assembly of claim 10, wherein the projection includes a pin that is removably attachable to the body, the pin being securable to the body by a set screw associated with the body.

12. A surgical aid assembly for attachment to a patient's bone, comprising:

an image tracker;

a device for stabilizing the image tracker to the patient's bone, the device including a body comprising:

a plurality of surfaces comprising:
- a top surface;
- a bottom surface;
- a first side surface; and
- a second side surface, wherein the first side surface and second side surface are longer than the top surface and bottom surface and wherein a longitudinal axis is parallel with the first side surface;

a first aperture disposed on said first side surface;

a second aperture disposed on at least one of the surfaces selected from the group consisting of:
- said bottom surface; and
- said second side surface;

a passageway between said first and second apertures, the passageway having an inner flange, an axis and a set screw operable with the passageway to secure said bone screw in place within the passageway, wherein the axis of the passageway obliquely traverses the longitudinal axis of the body; and a projection disposed on at least one of the surfaces selected from the group consisting of:
- said second side surface of said body; and
- said bottom surface of said body;

a mounting post disposed on said body and operable to releaseably attach the image tracker to said body; and a securing mechanism consisting of a single bone screw;

wherein said first and second apertures are both sized to receive said bone screw; and wherein said bone screw is adapted to be inserted through said passageway and into the patient's bone for temporarily stabilizing the image tracker.

13. The surgical aid assembly of claim 12, wherein the projection includes a pin that is removably attachable to the body, the pin being securable to the body by a set screw associated with the body.

* * * * *